United States Patent
Hettrick et al.

(10) Patent No.: US 7,065,398 B2
(45) Date of Patent: Jun. 20, 2006

(54) ATRIAL TACHYCARDIA TERMINATION SENSING

(75) Inventors: Douglas A. Hettrick, Blaine, MN (US); Jacqueline Mittelstadt, Milwaukee, WI (US)

(73) Assignee: Medtronic, Inc., Minneapolis, MN (US)

( * ) Notice: Subject to any disclaimer, the term of this patent is extended or adjusted under 35 U.S.C. 154(b) by 624 days.

(21) Appl. No.: 10/260,845

(22) Filed: Sep. 30, 2002

(65) Prior Publication Data

US 2004/0064160 A1    Apr. 1, 2004

(51) Int. Cl.
*A61B 5/452*    (2006.01)

(52) U.S. Cl. ...................................... 600/515

(58) Field of Classification Search ........ 600/508–510, 600/515, 518; 607/4–5, 9, 10, 14, 27, 28
See application file for complete search history.

(56) References Cited

U.S. PATENT DOCUMENTS

| | | | |
|---|---|---|---|
| 5,144,949 A | 9/1992 | Olson | 128/419 PG |
| 5,454,836 A | 10/1995 | van der Veen et al. | 607/9 |
| 5,730,142 A | 3/1998 | Sun et al. | 128/705 |
| 5,778,881 A | 7/1998 | Sun et al. | 128/696 |
| 5,792,192 A | 8/1998 | Lu | 607/14 |
| 6,129,745 A | 10/2000 | Sun et al. | 607/27 |
| 6,324,422 B1 | 11/2001 | Williams et al. | 600/510 |
| 6,819,955 B1 * | 11/2004 | Levine | 607/28 |

* cited by examiner

*Primary Examiner*—Robert E. Pezzuto
*Assistant Examiner*—Kristen Mullen
(74) *Attorney, Agent, or Firm*—Michael C. Soldner; Girma Wolde-Michael (57) ABSTRACT

Techniques for preventing inadvertent detection of AT termination may involve predicting potential undersensing of atrial events, and delaying detection of AT termination when undersensing of atrial events is predicted. For example, an implantable medical device may measure ventricular-atrial (VA) intervals of a heart rhythm using tracked atrial and ventricular events. The device calculates a slope of the series of the VA intervals, and estimates a prospective VA interval using the calculated slope and the most recently measured VA interval. The device determines whether the estimated VA interval is within a threshold range. When the estimated VA interval is outside of the threshold range, the device predicts possible undersensing of atrial events and delays detection of the AT episode termination. The delay detection of AT episode termination improves the accuracy of information collected by event counters.

32 Claims, 6 Drawing Sheets

ATRIAL TACHYCARDIA TERMINATION SENSING

TECHNICAL FIELD

The invention relates to cardiac pacing systems and, more particularly, to systems for delivering atrial pacing therapies to treat atrial tachycardia.

BACKGROUND

An arrhythmia is a disturbance in the normal rate, rhythm or conduction of the heartbeat. An atrial arrhythmia originates in the atria. Atrial tachycardia (AT), one form of atrial arrhythmia, is a condition in which the atria contract at a high rate, e.g., 100 or more beats per minute. Atrial fibrillation (AF), another form of atrial arrhythmia, is characterized by a chaotic and turbulent activation of atrial wall tissue. AT can lead to AF, which in turn can be life threatening.

Treatment for tachycardia may include anti-tachycardia pacing (ATP) or cardioversion, in which a train of high rate pulses or one or more high energy pulses is delivered to the heart in an attempt to restore a more normal rhythm. ATP is typically effective in converting stable atrial tachycardias to normal rhythm, and is often delivered via an implanted device. In many cases, a sequence of increasingly aggressive ATP therapies are applied until an episode of AT is terminated. Some implanted devices can be configured to discontinue ATP and immediately apply cardioversion in the event the AT degrades into AF.

SUMMARY

In general, the invention is directed to techniques for preventing inadvertent detection of AT termination. The techniques may involve predicting potential undersensing of atrial events, and delaying detection of AT termination when undersensing is predicted. Undersensing of atrial events may occur, for example, during the blanking interval following delivery of a ventricular pacing pulse. Due to undersensing, a continuing AT rhythm can be interpreted as a regular rhythm, resulting in detection of an AT termination. The predictive techniques described herein can be used to recognize undersensing, and thereby prevent inadvertent detection of AT termination.

An implantable medical device, for example, can be configured to track atrial events and ventricular events of a patient to monitor an AT episode. The implantable medical device uses the tracked atrial events and ventricular events to measure ventricular-atrial (VA) time intervals as an indication of an AT episode. According to some embodiments, a processor within the implantable medical device calculates the slope of a series of VA time intervals, and uses the calculated slope and a previous VA time interval to estimate a prospective VA time interval. The processor may determine whether the estimated VA time interval is within a threshold range.

For example, when the estimated VA time interval is greater than a current ventricular-ventricular (VV) time interval, the estimated VA time interval is outside of the threshold range. Further, when the estimated VA time interval is less than a blanking interval, the estimated VA time interval is outside of the threshold range. The processor recognizes the possibility of undersensing when the estimated VA time interval is outside of the threshold range. In this case, the processor delays detection of an AT episode termination upon predicting the possibility of undersensing of an atrial event. The process may delay the detection of AT episode termination for a defined time interval, a defined number of atrial events, or the like.

In one embodiment, the invention provides a method comprising tracking atrial events and ventricular events of a patient to monitor an atrial tachyarrhythmic (AT) episode, detecting possible undersensing of an atrial event, and delaying detection of a termination of the AT episode when possible undersensing is detected.

In another embodiment, the invention provides a device comprising a detector to detect atrial events and ventricular events of a patient and a processor to predict possible undersensing of an atrial event, and delay detection of a termination of an atrial tachyarrhythmic (AT) episode when possible undersensing is detected.

In an additional embodiment, the invention provides a computer-readable medium comprising instructions to cause a process to track atrial events and ventricular events of a patient to monitor an atrial tachyarrhythmic (AT) episode, predict possible undersensing of an atrial event, and delay detection of a termination of the AT episode when possible undersensing is detected.

In a further embodiment, the invention provides an implantable medical device comprising means for detecting atrial events and ventricular events of a patient, means for predicting possible undersensing of an atrial event, and means for delaying detection of atrial tachyarrhythmic (AT) episode termination when possible undersensing is predicted.

The invention can provide a number of advances in the art. In general the invention is capable of increasing the accuracy of AT episode terminations. Increasing the accuracy of AT episode terminations increases the reliability of information collected by event counters tracking AT episode information. More reliable information may increase the clinical utility of the information. For example, a physician may be able to better determine a set of ATP therapies to program into the implantable medical device for a patient, and identify which therapies programmed for a patient are successful and which are not. In addition, reliable AT episode terminations avoid inadvertent deviation from ATP escalation routines. For example, the implantable medical device may continue the escalation of ATP therapies instead of inadvertently restarting a new regimen of ATP therapies. Also, the duration of AT episodes may influence clinical decisions regarding prescription drug therapy, especially anticoagulation therapy.

The details of one or more embodiments of the invention are set forth in the accompanying drawings and the description below.

DETAILED DESCRIPTION

Figure 1:
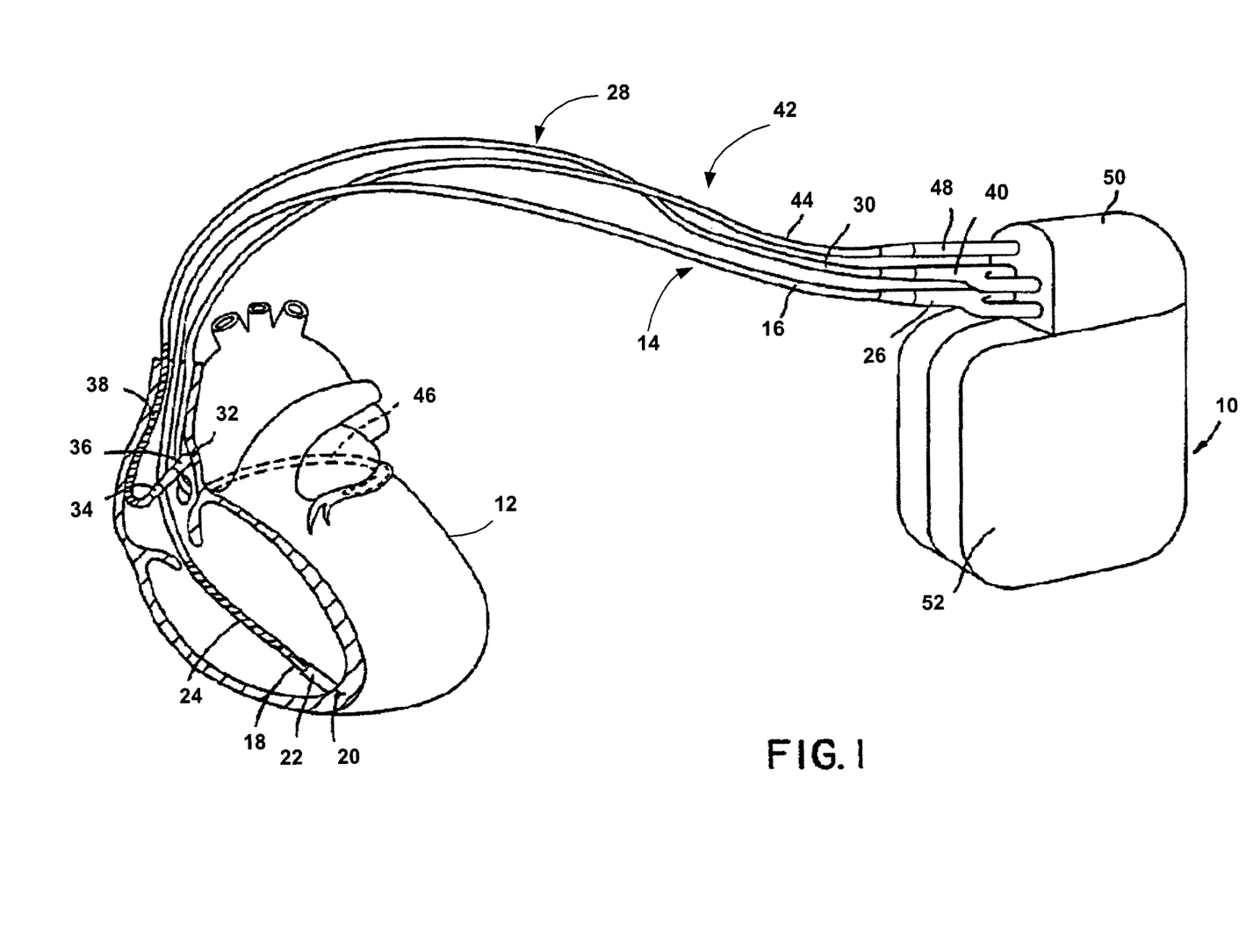
FIG. 1 is a diagram illustrating an implanted medical device useful in delivering anti-tachycardia pacing (ATP) therapies.

FIG. 1 is a diagram illustrating an implanted medical device 10 useful in delivering anti-tachycardia pacing (ATP) therapies. Device 10, shown in conjunction with a human heart 12, may be configured to deliver atrial pacing therapy as well as defibrillation shocks, and monitor the effect of the delivered atrial pacing therapy. As will be described, implanted medical device 10 can be configured to predict potential undersensing of atrial events, and delay detection of AT termination when undersensing is predicted. The specific structure of device 10 is described below for purposes of example, and should not be considered limiting of the invention as broadly embodied herein.

As shown in FIG. 1, device 10 may include a ventricular lead 14 having an elongated insulative lead body 16, carrying three concentric coiled conductors, separated from one another by tubular insulative sheaths. Located adjacent the distal end of ventricular lead 14 are a ring electrode 18, an extendable helix electrode 20, mounted retractably within an insulative electrode head 22 and an elongated coil electrode 24. Each of electrodes 18, 20, 22, and 24 is coupled to one of the coiled conductors within lead body 16. Electrodes 18, 20, 22, and 24 can be used for both cardiac pacing and sensing of ventricular depolarizations, often referred to as ventricular events. At the proximal end of ventricular lead 14 is a bifurcated connector 26 that carries three electrical connectors, each coupled to one of the coiled conductors.

An atrial lead 28 includes an elongated insulative lead body 30, carrying three concentric coiled conductors, separated from one another by tubular insulative sheaths. Located adjacent the J-shaped distal end of atrial lead 28 are a ring electrode 32 and an extendable helix electrode 34, mounted retractably within an insulative electrode head 36. Each of electrodes 32, 34, and 36 is coupled to one of the coiled conductors within lead body 30. Electrodes 32, 34, and 36 are employed for atrial pacing and for sensing atrial depolarizations, often referred to as atrial events. An elongated coil electrode 38 is provided proximal to ring electrode 32 and coupled to the third conductor within lead body 30. At the proximal end of lead 28 is a bifurcated connector 40 that carries three electrical connectors, each coupled to one of the coiled conductors.

A coronary sinus lead 42 includes an elongated insulative lead body 44, carrying one coiled conductor coupled to an elongated coiled defibrillation electrode 46. Electrode 46, illustrated in broken outline, is located within the coronary sinus and great vein of the heart. At the proximal end of lead 42 is a connector plug 48 that carries an electrical connector, coupled to the coiled conductor. Leads 14, 28, and 42 are inserted into a connector block 51 associated with device 10. Device 10 has an outer housing 52 that may function as a subcutaneous defibrillation electrode that defibrillates either the atria or ventricles.

Figure 2:
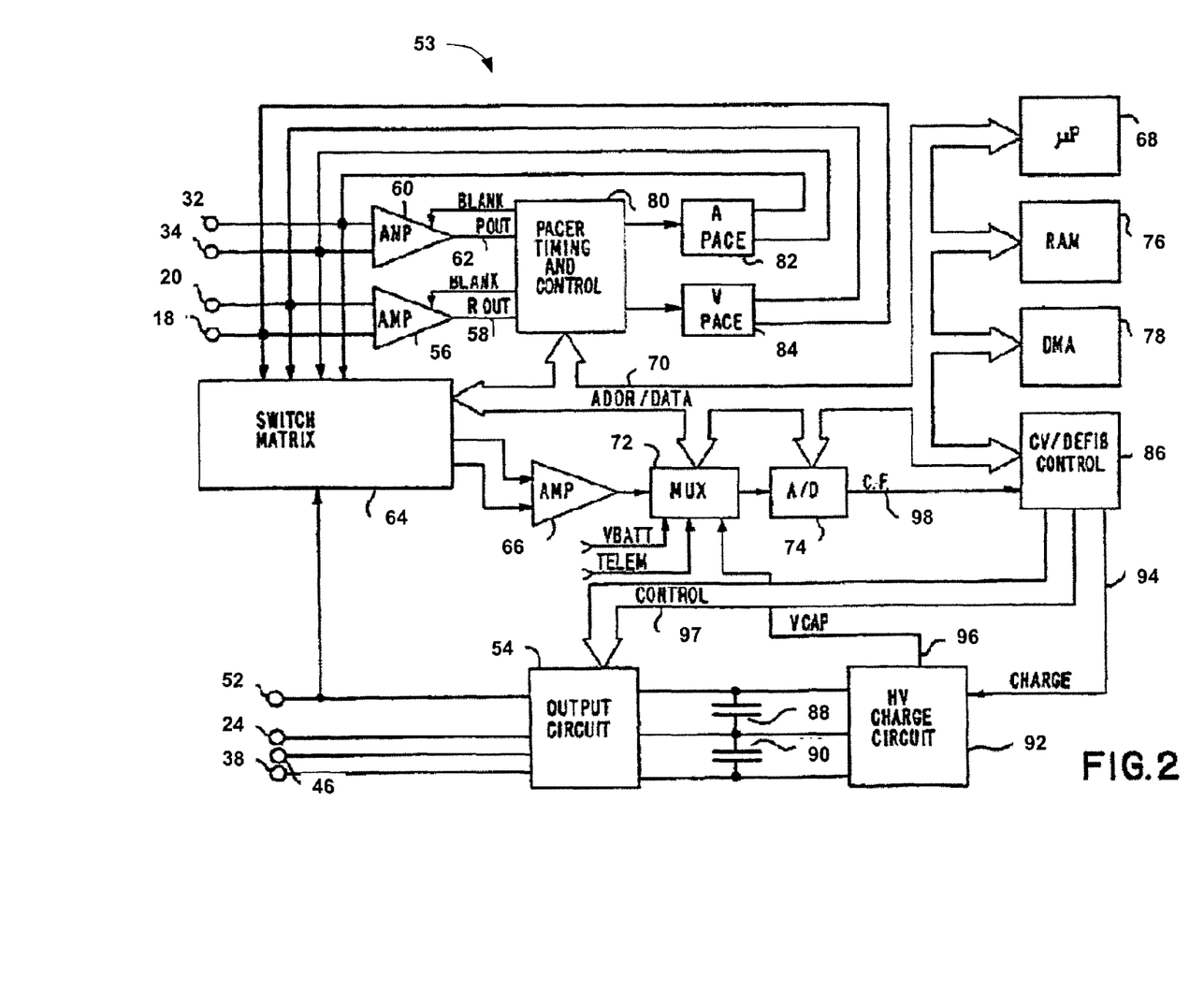
FIG. 2 is a functional schematic diagram illustrating a system capable of delivering ATP therapies.

FIG. 2 is a functional schematic diagram illustrating a system 53 capable of delivering ATP therapies. System 53 may further be capable of delaying detection of an AT episode termination when undersensing of an atrial event is predicted. The system may be implemented within device 10 of FIG. 1, and may take the form of an implantable device that integrates various pacemaker/cardioverter/defibrillator functions. The diagrams of FIGS. 1 and 2 should be taken as exemplary of the type of device in which the invention may be embodied, however, and not as limiting of the invention as broadly embodied herein. For example, the invention may be practiced in a wide variety of device implementations, including devices providing therapies for treating atrial arrhythmias or both atrial and ventricular arrhythmias. In addition, the invention may be practiced in anti-tachycardia pacemakers that do not provide cardioversion or defibrillation, as well as devices that deliver different forms of anti-arrhythmia therapies such as nerve stimulation or drug administration. In addition, certain features of the invention may be useful in traditional anti-bradycardia devices with atrial episode detection.

In the example of FIG. 2, electrode 52 represents the uninsulated portion of the housing of device 10, which may function as a defibrillation electrode. Electrodes 24, 38, 46, and 52 are coupled to high voltage output circuit 54. Electrodes 18 and 20 are coupled to R-wave amplifier 56, which preferably takes the form of an automatic gain controlled amplifier providing an adjustable sensing threshold as a function of the measured R-wave amplitude. A signal is generated on R-out line 58 whenever the signal sensed between electrodes 18 and 20 exceeds the present sensing threshold.

Electrodes 32 and 34 are coupled to the P-wave amplifier 60, which also may take the form of an automatic gain controlled amplifier providing an adjustable sensing threshold as a function of the measured P-wave amplitude. A signal is generated on P-out line 62 when the signal sensed between electrodes 32 and 34 exceeds the sensing threshold. Switch matrix 64 selects which of the available electrodes are coupled to wide band amplifier 66 for use in digital signal analysis. Selection of electrodes is controlled by a controller, which may take the form of a microprocessor 68. Microprocessor 68 controls selection of electrodes by switch matrix 64 via data/address bus 70. Signals from the electrodes selected for coupling to bandpass amplifier 66 are provided to multiplexer 72 and thereafter converted to multi-bit digital signals by A/D converter 74, for storage in random access memory (RAM) 76 under control of direct memory access circuit 78.

Microprocessor 68 may employ digital signal analysis techniques to characterize the digitized signals stored in random access memory 76 to recognize and classify the heart rhythm using any of a variety of known signal processing methods. In particular, microprocessor 68 may implement a detector that tracks the cycle length and regularity of the heart rhythm during an AT episode. For example, the detector may track atrial events and ventricular events of the patient to monitor the AT episode. From the atrial and ventricular events, microprocessor 68 may, for example, detect a termination of the AT episode. Further, microprocessor 68 may predict possible undersensing and delay detection of AT episode termination when undersensing is predicted. The remainder of the circuitry illustrated in FIG. 2 is dedicated to the provision of cardiac pacing, cardioversion, and defibrillation therapies.

Pacer timing/control circuitry 80 may include programmable digital counters that control the basic time intervals associated with DDD, VVI, DVI, VDD, AAI, DDI and other modes of single and dual chamber pacing well known to the art. More particularly, circuitry 80 is configured to control escape intervals associated with anti-tachyarrhythmia pacing in the atrium or both the atrium and ventricle. To treat an episode of tachyarrhythmia, circuitry 80 may employ known ATP therapies.

Intervals defined by pacing circuitry 80 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 68, in response to stored data in memory 76, and are communicated to the pacing circuitry 80 via address/data bus 70. Circuitry 80 also determines the amplitude of the cardiac pacing pulses under control of microprocessor 68.

During pacing, the escape interval counters within pacer timing/control circuitry 80 are reset upon sensing of R-waves and P-waves, and in accordance with the selected mode of pacing on time-out trigger generation of pacing pulses by pacer output circuits 82 and 84, which are coupled to electrodes 18, 20, 32, and 34. The escape interval counters are also reset upon generation of pacing pulses, and thereby control the basic timing of cardiac pacing functions, including anti-tachyarrhythmia pacing.

The durations of the intervals defined by the escape interval timers are determined by microprocessor 68 via data/address bus 70. The value of the count present in the escape interval counters when reset by sensed R-waves and P-waves may be used to measure the durations of R—R intervals, P—P intervals, P-R intervals and R-P intervals, also known as VV intervals, AA intervals, AV intervals, and VA intervals. The VA interval, for example, is the length of time between a ventricular event and one or more atrial events following the ventricular event. Microprocessor 68 may use these measured intervals to predict the possibility of undersensing. The resulting measurements can be stored in memory 76 and used to detect tachyarrhythmias. To detect tachycardia and associated cycle length and regularity, the invention may employ any of a variety of known tachycardia detection algorithms.

In the event that an AT episode is detected, and an anti-tachyarrhythmia pacing regimen is desired, microprocessor 68 prescribes appropriate timing intervals for controlling generation of anti-tachyarrhythmia pacing therapies by pacer timing and control circuitry 80. In particular, the timing intervals control the operation of the escape interval counters in circuitry 80 and define refractory periods during which detection of R-waves and P-waves are ineffective to restart the escape interval counters.

In operation, microprocessor 68 selects one of several ATP therapy sequences based on characteristics of the heart rhythm, such as cycle length and regularity. In the event that generation of a cardioversion or defibrillation pulse is required, microprocessor 68 employs the escape interval counter to control timing of cardioversion and defibrillation pulses, as well as associated refractory periods. In response to the detection of atrial or ventricular fibrillation or tachyarrhythmia requiring a cardioversion pulse, microprocessor 68 activates cardioversion/defibrillation control circuitry 86, which initiates charging of the high voltage capacitors 88 and 90 via charging circuit 92, under control of high voltage charging control line 94. The voltage on high voltage capacitors 88, 90 is monitored via VCAP line 96, which is passed through multiplexer 72 and in response to reaching a predetermined value set by microprocessor 68, results in generation of a logic signal on Cap Full (CF) line 98, terminating charging. Thereafter, timing of the delivery of the defibrillation or cardioversion pulse is controlled by circuitry 86 via control bus 97. Following delivery of the fibrillation or tachycardia therapy, microprocessor 68 then returns device 10 to cardiac pacing and awaits the next pacing event or sensed atrial or ventricular depolarization.

Device 10 may be configured to apply an increasingly aggressive regimen of therapies. Upon initial detection of an AT, a sequence of atrial ATP therapies may be selected and delivered to the atrium. The sequence defines an order of ATP therapies to be applied in attempts to terminate the AT episode. The ATP therapies will typically be ordered from least to most aggressive. If the AT persists following application of the first ATP therapy, microprocessor 68 controls circuitry 80 to apply the next ATP therapy in the sequence. If the AT is not terminated, treatment continues using the other ATP therapies in the sequence. Further, microprocessor 68 may continue treatment using the other ATP therapies when the detection of the termination of the AT episode is delayed due to possible undersensing. In other words, inadvertent AT episode termination is avoided and thus a new regimen of ATP therapies is not inadvertently restarted. For instance, microprocessor 68 may apply the next ATP therapy in the regimen instead of starting from the beginning of the regimen again.

Figure 3:
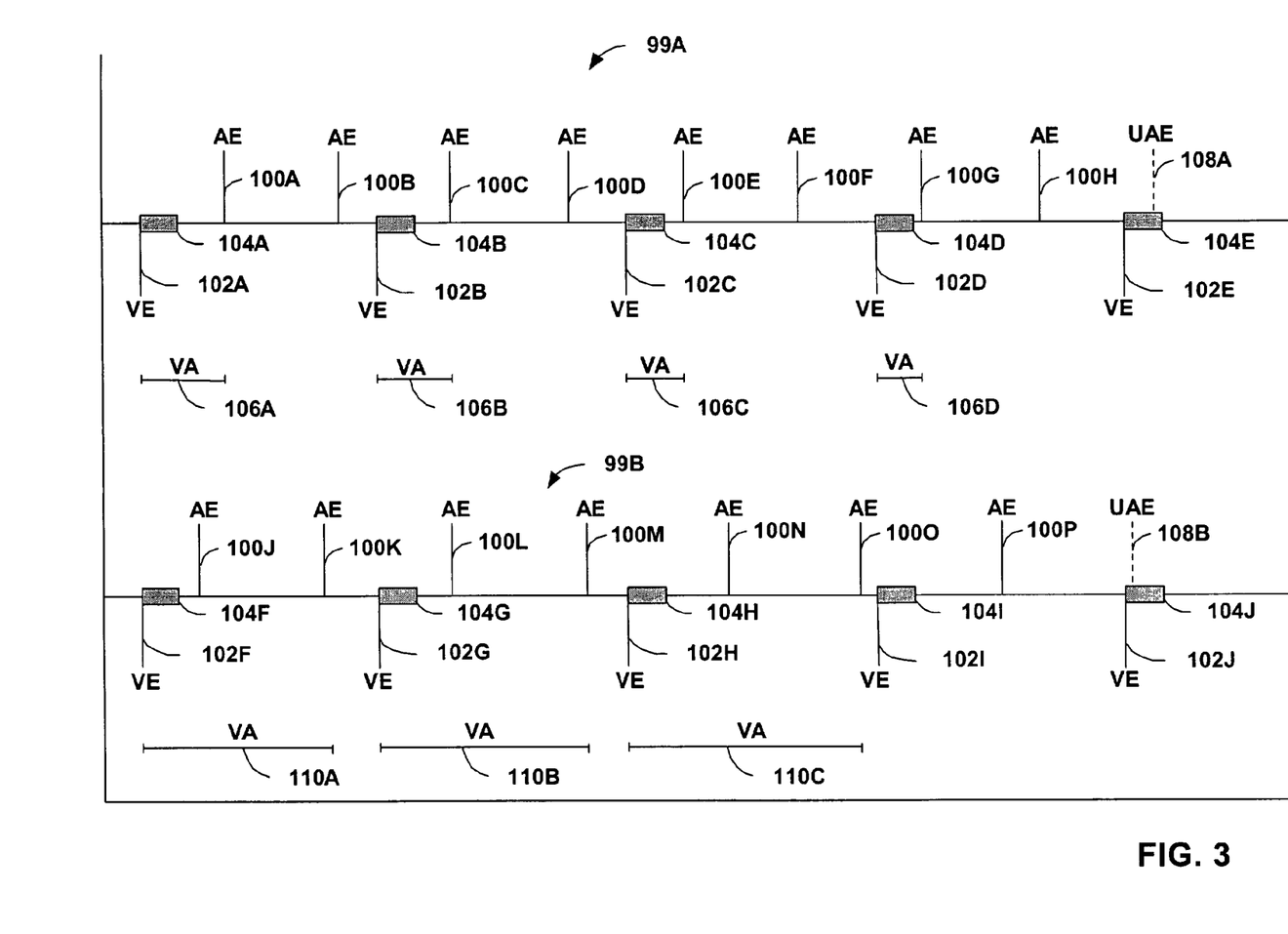
FIG. 3 is a marker channel diagram illustrating AT episodes in which undersensing of atrial events occurs.

FIG. 3 is a marker channel diagram illustrating exemplary AT episodes 99A and 99B ("99") in which undersensing of atrial events occurs. An implantable medical device, such as implanted medical device 10, tracks atrial events (AEs) 100A–100P ("100") and ventricular events (VEs) 102A–102J ("102"). Ventricular events 102, for example, may be ventricular pacing pulses administered by implanted medical device 10. Alternatively, ventricular events 102 may be naturally occurring, i.e., intrinsic, ventricle depolarizations or contractions. Following paced ventricular events 102 are blanking intervals 104A–104J ("104") in which the sensitivity of detectors that detect atrial events 100 may be decreased, e.g., to avoid saturation. During a blanking interval 104, implanted medical device 10 may fail to sense ("undersense") one of atrial events 100 due to the reduced sensitivity of the detector.

In the example of the marker channel diagram of FIG. 3, two atrial events 100 occur between each of ventricular events 102, indicating a heart rhythm experiencing an AT episode. The fast atrial rate and the regular ventricular rate may not be phase locked, i.e., atrial events 100 may shift with respect to ventricular events 102. In the marker channel diagram of AT episode 99A, the atrial rate shifts such that atrial events 100 shift toward the respective ventricular events 102 from which a respective VA time interval 106 is measured. For example, atrial event 100C shifts toward ventricular event 102B, atrial event 100E shifts even further toward ventricular event 102C, and so forth. The result of the shift is smaller VA time intervals 106 between each of ventricular events 102 and the following atrial events 100.

In the example of AT episode 99A, only VA intervals 106 for atrial events 100 immediately following each of ventricular events 102 are shown, i.e. atrial events 100A, 100C, 100E, and 100G. As the shift of atrial events 100 with respect to ventricular events 102 continues, atrial events 100 immediately following a respective one of ventricular events 102 begin to approach the blanking interval 104 of the respective ventricular event 102. When atrial events 100 immediately following respective ventricular event 102 shift such that atrial events 100 aligns with blanking intervals 104 associated with the respective ventricular event 102, an undersensed atrial event (UAE) 108A may occur. In other words, some atrial events 100 may be hidden by the blanking interval, leading to undersensing.

In the marker channel diagram of AT episode 99B, the atrial rate shifts in the opposite direction as in AT episode 99A, i.e., the atrial rate shifts such that atrial events 100 shift away from the respective one of ventricular events 102 from which the respective VA time interval 108 is measured. For example, atrial event 100K shifts toward ventricular event 102G, atrial event 100M shifts even further toward ventricular event 102H, and so forth. The result of the shift is larger VA time intervals 110 between each of ventricular events 102 and the following atrial events 100. As the shift of atrial events 100 with respect to ventricular events 102 continues to occur, atrial events 100 occurring furthest from the respective ventricular event 102, i.e., atrial events 100K, 100M, and 100O, of an associated VA interval 110 begin to approach the blanking intervals 104 of the next ventricular event 102. When atrial events 100 shift into blanking intervals 104 associated with the next ventricular event 102, an undersensed atrial event (UAE) 108B may occur.

The undersensing of atrial events 100 may only last for a few beats, but within those few beats implanted medical device 10 may inadvertently detect AT episode termination when in fact the AT episode is still present. Early detection of an AT episode termination may cause the AT episode duration and frequency data collected by event counters to be inaccurate. For example, an AT episode that is incorrectly detected as terminated will lead to a low duration time for the actual AT episode, and possibly to an inaccurate number of occurrence data if the AT episode is detected again as soon as undersensing is not present. An algorithm for predicting undersensing and delaying detection of AT episode termination, described in detail below, increases the reliability of AT episode termination detection, and increases the clinical utility of data collected by the event counters.

Implanted medical device 10 may use the sensed atrial events 100 and sensed ventricular events 102 to measure VA time intervals 106 and 110 to predict possible undersensing of atrial events. For example, microprocessor 68 of implanted medical device 10 may calculate a slope of a series of VA time intervals 106, 110, estimate a prospective VA interval based on a previous VA interval 106, 110 and the calculated slope, and predict possible undersensing of an atrial event when the estimated VA interval is outside of a predetermined range. Implanted medical device 10 may delay the detection of AT episode termination long enough for atrial events 100 to no longer occur within blanking intervals 104 of ventricular events 102. For example, implantable medical device 10 may delay the detection of AT episode termination for a defined amount of time, for instance 10 seconds, or for a defined number of atrial events. Device 10 may also use the calculated slope to estimate the amount of time to delay detection on an event-by-event basis. For example, the delay could be calculated as 180/m. In this case, in effect, device 10 predicts when the blanked atrial event will emerge from blanking. After the defined delay, implanted medical device 10 either continues to detect the AT episode or accurately detects AT episode termination.

Figure 4:
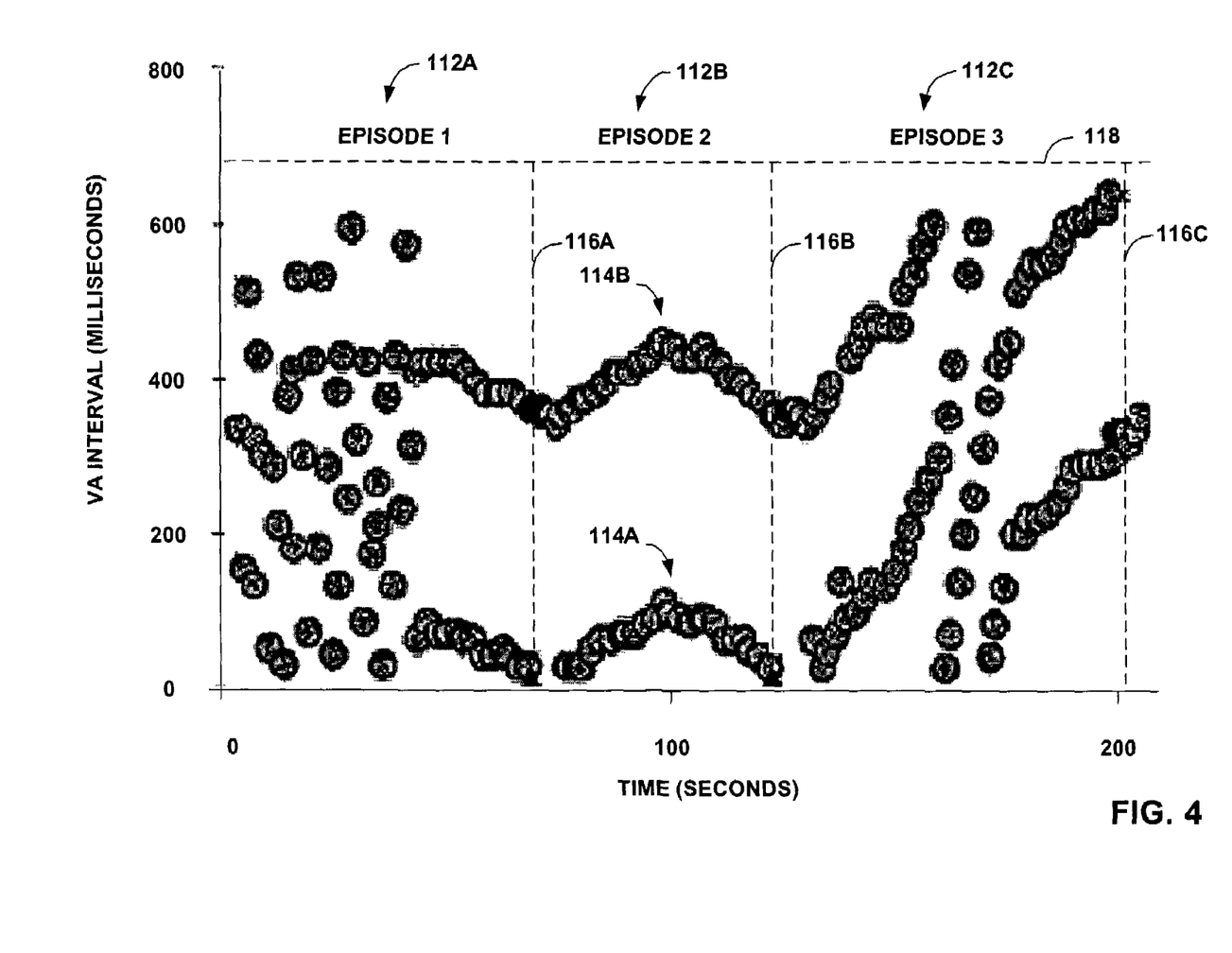
FIG. 4 is a graph illustrating an exemplary plot of a series of ventricular-atrial (VA) time intervals during consecutive AT episodes of a patient.

FIG. 4 is a graph illustrating an exemplary plot of a series of VA time intervals during consecutive AT episodes 112A–112C ("112") for a particular patient. In the graph of FIG. 4, the patient suffers from three consecutive AT episodes 112. In reality, these three episodes were part of a single, longer episode. The termination of each AT episode 12 was inappropriately detected because of undersensing during the blanking interval following a preceding ventricular pacing pulse.

An implanted medical device, such as implanted medical device 10, configured in accordance with the principles of the invention, can predict the possibility of undersensing, and delay detection of AT episode termination upon detecting the possibility of undersensing. In particular, implanted medical device 10 may use a slope of the series of VA time intervals to predict the possibility of undersensing. An example of a suitable equation to calculate the slope of the series of VA intervals is shown below:

$$\text{slope}=[(VA_n-VA_{n-2})+(VA_{n-2}-VA_{n-4})+(VA_{n-4}-VA_{n-6})]/3 \quad (1)$$

In the equation above, $VA_n$ represents the most recently measured VA time interval of the series of VA time intervals. $VA_{n-2}$ represents the third most recently measured VA time interval, $VA_{n-4}$ represents the fifth most recently measured VA time interval, and $VA_{n-6}$ represents the seventh most recently measured VA time interval. The equation for the slope of the series of VA time intervals uses every other VA time interval. This is due to the nature of atrial events 100 and ventricular events 102 during AT episodes 112. In the example of FIG. 3 described above, two atrial events 100 correspond with each of ventricular events 102, one early within the ventricular-ventricular (VV) time interval and one late within the VV time interval. The VA time intervals for the first of the two atrial events 100 plot to form a first line 114A. The VA time intervals for the second of the two atrial events 100 plot to form a second line 114B. In this manner, using every other VA interval to calculate the slope of the series of VA intervals results in the slope of one of lines 114.

The slopes of the resulting lines 114A, 114B are used to calculate a prospective VA time interval, i.e., $VA_{n+2}$, as follows:

$$VA_{n+2}=VA_n+\text{slope} \quad (2)$$

Implanted medical device 10 and, more specifically, microprocessor 68 may predict possible undersensing by determining whether $VA_{n+2}$ is within an appropriate range. Specifically, undersensing may be possible when $VA_{n+2}$ exceeds a maximum threshold value or falls below a minimum threshold value. For example, if the value of $VA_{n+2}$ is less than an expected blanking interval, atrial undersensing is possible because the expected atrial event is predicted to occur within the blanking interval. A blanking interval, for example, may last as long as 25 milliseconds or sometimes longer.

In the exemplary plot of FIG. 4, $VA_{n+2}$ falls below the minimum threshold at line 116A and 116B. Line 116A and 116B also illustrate the area in which inappropriate detection of the termination of the AT episode occurred. In this manner, implanted medical device 10 can predict possible atrial undersensing in order to prevent inappropriate detection of the termination of the AT episode. In another example, if the value of $VA_{n+2}$ exceeds a threshold value, such as the current VV time interval represented by line 118, the atrial event 100 occurring late in the VV interval crosses into the next VV interval and may occur during the blanking interval of the next VV interval, making undersensing possible. In the exemplary plot of FIG. 4, $VA_{n+2}$ exceeds the current VV time interval at line 116C. Line 116C also represents another area in which inappropriate detection AT episode termination occurred. Upon predicting possible undersensing, whether it be from $VA_{n+2}$ exceeding a maximum threshold or falling below a minimum threshold, microprocessor 68 delays detection AT episode termination.

Figure 5:
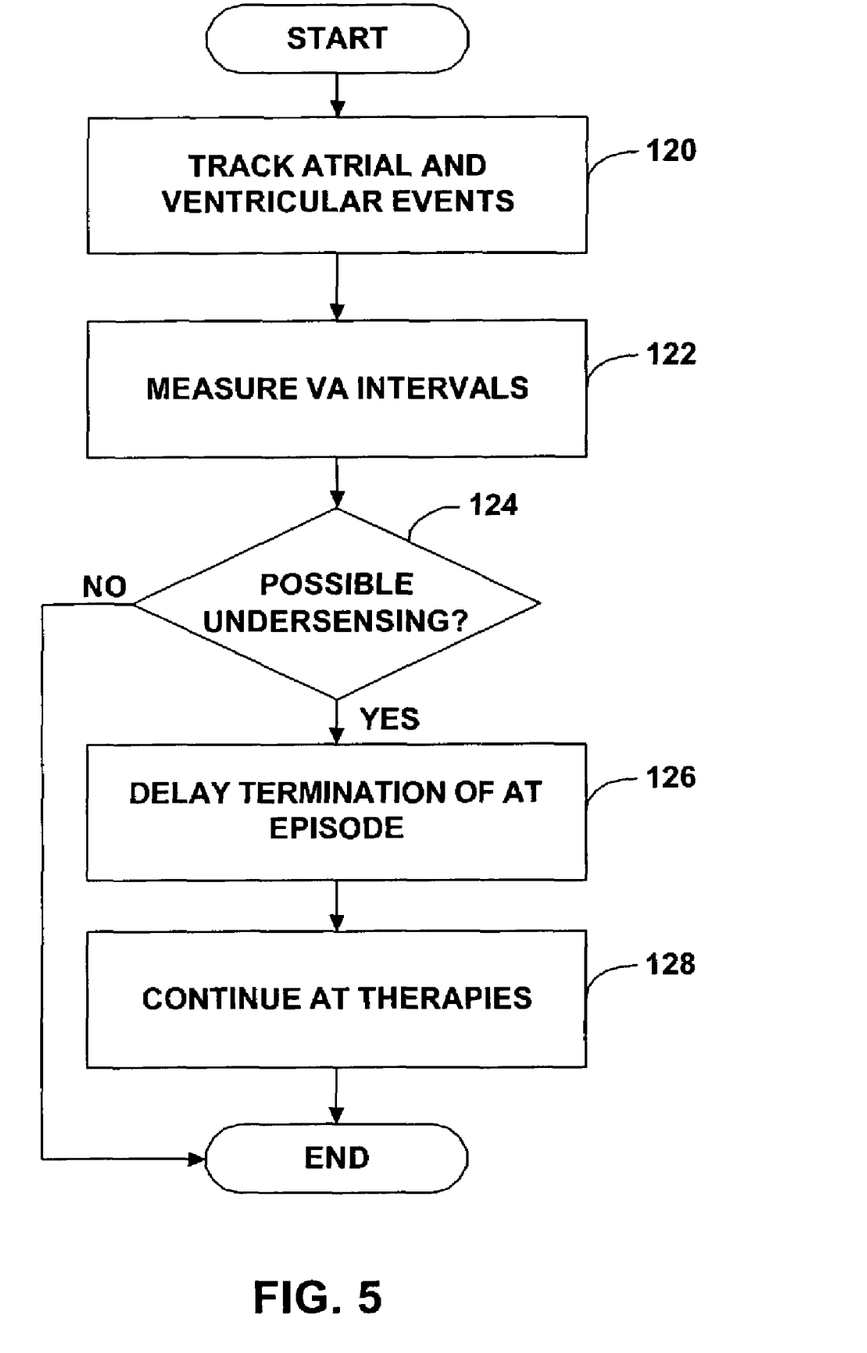
FIG. 5 is a flow diagram illustrating a technique for preventing inadvertent detection of AT termination.

FIG. 5 is a flow diagram illustrating a technique for preventing inadvertent detection of AT termination. Implantable medical device 10 tracks atrial events and ventricular events to monitor an AT episode (120). Implantable medical device 10 may, for example, track atrial events with a first detector and ventricular events with a second detector as described in FIG. 1. Alternatively, implantable medical device 10 may track atrial events and ventricular events with a single detector.

A microprocessor 68 within implantable medical device 10 may calculate VA intervals using the measured atrial events and ventricular events (122). Microprocessor 68 predicts whether undersensing is probable using the calculated VA intervals (124). For example, microprocessor 68 may determine whether an estimate of a prospective VA interval is within a threshold range. When undersensing is probable, microprocessor 68 delays detection of AT episode termination in order to accommodate the effects of undersensing of atrial events (126). For example, microprocessor 68 may delay the detection AT episode termination for a certain length of time or for a certain number of atrial events. Implanted medical device 10 continues to apply AT therapies in accordance with the regimen of therapies (128). When undersensing is not probable, microprocessor continues to monitor the AT episode and, more specifically, continues to monitor prospective VA intervals.

Figure 6:
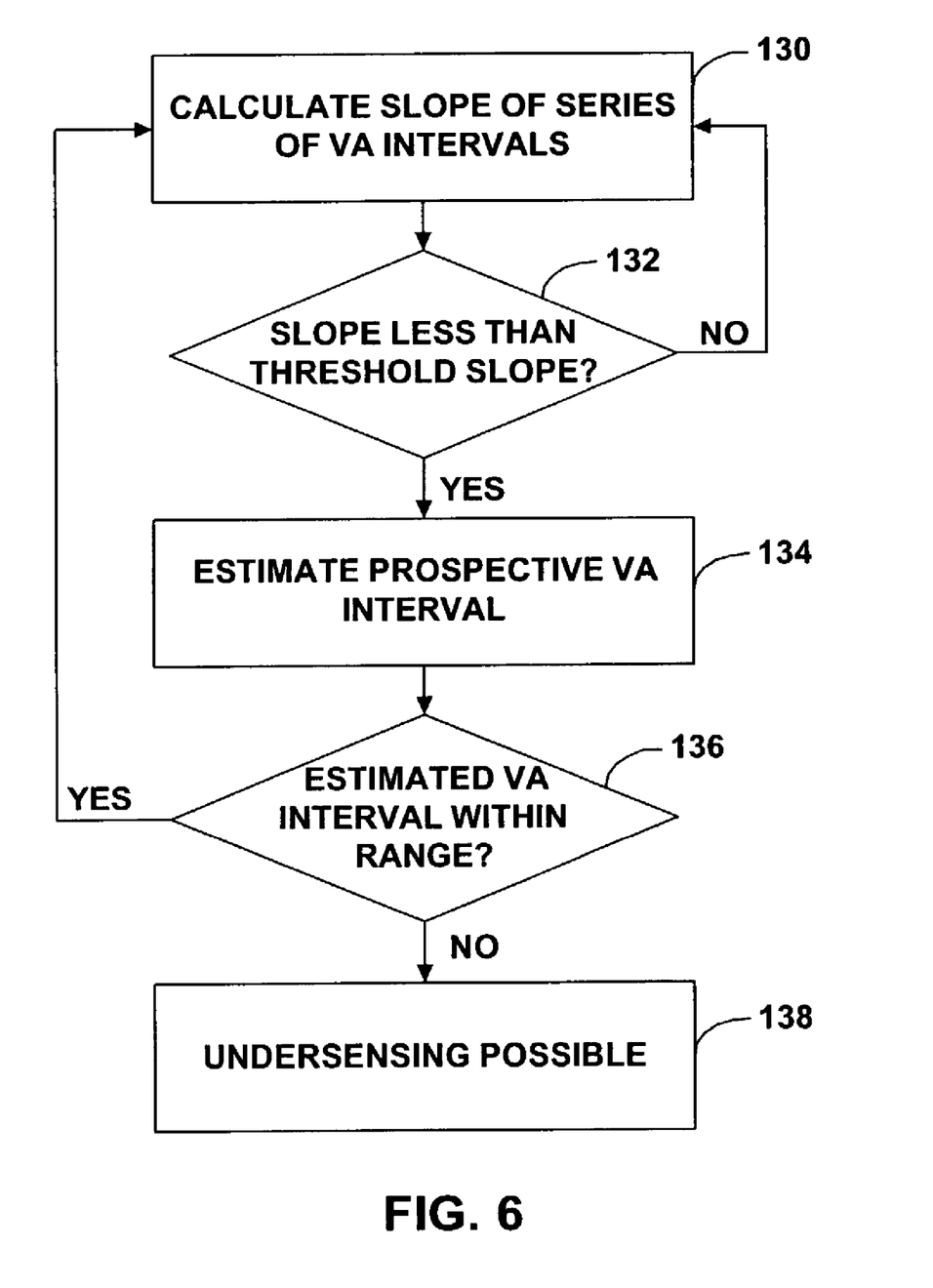
FIG. 6 is a flow diagram illustrating prediction of possible undersensing of atrial events using an estimate of a prospective VA time interval.

FIG. 6 is a flow diagram illustrating prediction of possible undersensing during an AT episode, e.g., by microprocessor 68 of implantable medical device 10. Microprocessor 68 calculates a slope of a series of VA intervals (130). Microprocessor 68 may calculate the slope of the series of VA intervals using equation (1). Although in equation (1) microprocessor 68 only uses four VA time intervals from the series of time intervals to determine the slope, microprocessor 68 may determine the slope of the series of VA time intervals using any number of VA time intervals from the series. Further, the slope of the VA time intervals may be calculated using any algorithm.

Microprocessor 68 determines whether the slope is less than a threshold slope (132). For example, the threshold slope may be approximately 60. When the slope is larger than approximately 60, microprocessor 68 continues to calculate the slope of the series of VA intervals. A slope that is larger than 60 may indicate that the underlying atrial arrhythmia is very irregular and thus unlikely to result in consistent transient, or that the atrial arrhythmia is conducted to the ventricle with an integral ratio greater than 2:1, in which case microprocessor 68 may detect the continuation of the AT episode even with undersensing occurring. Microprocessor 68 may, instead of comparing the slope with the threshold slope, may compare VA interval differences used to calculate the slope with a threshold value. For example, microprocessor may determine whether the absolute value of each of the VA differences, i.e., $|(VA_n-VA_{n-2})|$, $|(VA_{n-2}-VA_{n-4})|$, and $|(VA_{n-4}-VA_{n-6})|$ is less than 60. When each of the VA interval differences is less than 60, the slope is less than 60.

When the slope of the series of VA intervals is less than the slope threshold, microprocessor 68 estimates the prospective VA interval (134). Microprocessor 68 may estimate the prospective VA interval using at least one of the measured VA intervals and the calculated slope. For example, microprocessor 68 may estimate the prospective VA interval using equation (2).

Microprocessor 68 determines whether the estimated VA interval is within a threshold range (136). The threshold range may range from the width of the blanking interval of the ventricular event to a current VV interval. For instance, when the estimated VA interval is less than the blanking interval of a ventricular event, the VA interval may be outside of the threshold range. Further, when the estimated VA interval is greater than the current VV interval, the estimated VA interval may be outside of the threshold range. When the estimated VA time interval is within the threshold range, microprocessor 68 continues to calculate the slope of the series of VA intervals.

When the estimated VA time interval is not within the threshold range, i.e., falls below the blanking interval length or exceeds the current VV time interval, microprocessor 68 predicts possible undersensing (138).

Various embodiments of the invention have been described. These embodiments are illustrative of the practice of the invention. Various modifications may be made without departing from the scope of the claims. The methods and structures of the invention may be applied to implantable devices as well as external devices. For example, the invention may be applied to an external device that senses AT episodes in the presence of ventricular pacing. The ventricular pacing may be delivered by the external device, another external device, or an internal device, such as the implantable device described above. These and other embodiments are within the scope of the following claims.

What is claimed is:

1. A method comprising:
    tracking atrial events and ventricular events of a patient to monitor an atrial tachyarrhythmic (AT) episode;
    predicting possible undersensing of an atrial event; and
    delaying detection of AT episode termination when possible undersensing is predicted.

2. The method of claim 1, wherein tracking atrial and ventricular events includes:
    tracking ventricular-atrial (VA) time intervals; and
    tracking ventricular-ventricular (VV) time intervals.

3. The method of claim 1, wherein predicting possible undersensing of an atrial event includes:
    tracking ventricular-atrial (VA) time intervals;
    calculating a slope of a series of the VA intervals;
    estimating a prospective VA time interval based on a previous VA time interval and the calculated slope; and
    predicting possible undersensing of an atrial event when the estimated prospective VA time interval is outside of a range.

4. The method of claim 3, wherein calculating the slope of a series of the VA time intervals includes calculating the slope of a series of the VA time intervals using the equation $$m=[(VA_n-VA_{n-2})+(VA_{n-2}-VA_{n-4})+(VA_{n-4}-VA_{n-6})]/3,$$

wherein m represents the slope, $VA_n$ represents the most recent measured VA time interval of the series of VA time intervals, $VA_{n-2}$ represents the third most recent measured VA time interval, $VA_{n-4}$ represents the fifth most recent measured VA time interval, and $VA_{n-6}$ represents the seventh most recent measured VA time interval.

5. The method of claim 4, wherein estimating a prospective VA time interval based on a previous VA time interval and the calculated slope includes estimating a prospective VA time interval according to the equation $$VA_{n+2}=VA_n+m,$$

wherein $VA_{n+2}$ is the prospective VA time interval, $VA_n$ is the most recent previous VA time interval, and m is the calculated slope.

6. The method of claim 3, further comprising predicting possible undersensing of an atrial event when the estimated prospective VA interval exceeds or falls below a threshold.

7. The method of claim 6, further comprising:
    tracking ventricular-ventricular (VV) time intervals; and
    predicting possible undersensing of an atrial event when the estimated prospective VA interval exceeds a current VV interval.

8. The method of claim 6, further comprising predicting possible undersensing of an atrial event when the estimated prospective VA interval is less than a blanking interval.

9. The method of claim 8, wherein the blanking interval is approximately 25 milliseconds.

10. The method of claim 3, further comprising:
calculating a difference between previous VA intervals; and
predicting possible undersensing of an atrial event when the calculated difference between previous VA intervals is less than a threshold value.

11. The method of claim 10, wherein the threshold value is approximately 60.

12. The method of claim 3, further comprising:
comparing the slope of the VA intervals with a threshold slope; and
predicting possible undersensing of an atrial event when the slope is less than the threshold slope.

13. The method of claim 12, wherein the threshold slope is approximately 60.

14. The method of claim 1, wherein delaying detection of AT episode termination includes delaying detection of AT episode termination for a defined time interval.

15. The method of claim 1, wherein delaying detection of AT episode termination includes delaying detection of AT episode termination for a defined number of atrial events.

16. The method of claim 1, wherein predicting possible undersensing of an atrial event includes predicting possible undersensing of an atrial event within a blanking interval.

17. A computer-readable medium comprising instructions to cause a processor to:
track atrial events and ventricular events of a patient to monitor an atrial tachyarrhythmic (AT) episode;
predict possible undersensing of an atrial event; and
delay detection of AT episode termination when undersensing is predicted.

18. The computer-readable medium of claim 17, wherein instructions to predict possible undersensing include instructions to cause the processor to:
track ventricular-atrial (VA) time intervals;
calculate a slope of a series of the VA intervals;
estimate a prospective VA time interval based on a previous VA time interval and the calculated slope; and
predict possible undersensing of an atrial event when the estimated VA time interval is outside of a range.

19. The computer-readable medium of claim 18, further comprising instructions to cause the processor to predict possible undersensing of an atrial event when the estimated prospective VA time interval exceeds or falls below a threshold.

20. The computer-readable medium of claim 19, further comprising instructions to cause the processor to:
track ventricular-ventricular (VV) time intervals; and
predict possible undersensing of an atrial event when the estimated prospective VA interval exceeds a current VV interval.

21. The computer-readable medium of claim 19, further comprising instructions to cause the processor to predict possible undersensing of an atrial event when the estimated prospective VA time interval is less than a blanking interval.

22. The computer-readable medium of claim 17, wherein instructions to delay detection of AT episode termination includes instructions to cause the processor to delay detection of AT episode termination for a defined time interval.

23. The computer-readable medium of claim 17, wherein instructions to delay detection of AT episode termination includes instructions to cause the processor to delay detection of AT episode termination for a defined number of atrial events.

24. An implantable medical device comprising:
means for detecting atrial events and ventricular events of a patient;
means for predicting possible undersensing of an atrial event; and
means for delaying detection of atrial tachyarrhythmic (AT) episode termination when possible undersensing is predicted.

25. The device of claim 24, wherein the detecting means tracks ventricular-atrial (VA) time intervals and ventricular-ventricular (VV) time intervals.

26. The device of claim 24, wherein the detecting means tracks ventricular-atrial (VA) time intervals, and the predicting means calculates a slope of a series of the VA intervals, estimates a prospective VA time interval based on a previous VA time interval and the calculated slope, and predicts possible undersensing of an atrial event when the estimated prospective VA time interval is outside of a range.

27. The device of claim 26, wherein the detecting means tracks ventricular-ventricular (VV) time intervals and predicts possible undersensing of an atrial event when the estimated prospective VA time interval exceeds a current VV interval.

28. The device of claim 26, wherein the predicting means predicts possible undersensing of an atrial event when the estimated prospective VA time interval is less than a blanking interval.

29. The device of claim 24, wherein the delaying means delays the detection of AT episode termination by one of a defined time interval or a defined number of atrial events.

30. The device of claim 24, wherein the detecting means includes:
a first detector to detect atrial events; and
a second detector to detect ventricular events.

31. The device of claim 24, further comprising an event counter to record information for AT episodes.

32. The device of claim 31, wherein the information recorded by the event counter includes duration of the AT episode and the number of AT episodes.

* * * * *